US007419965B2

(12) United States Patent
Herrmann et al.

(10) Patent No.: US 7,419,965 B2
(45) Date of Patent: Sep. 2, 2008

(54) NUCLEOTIDE LIPID ESTER DERIVATIVES

(75) Inventors: Dieter Herrmann, Heidelberg (DE); Brigitte Heckl-Oestreicher, Heidelberg (DE); Christoph Mueller, Birkenau (DE); Christian Lutz, Dossenheim (DE); Robert Voigt, Heidelberg (DE); William E. Bauta, San Antonio, TX (US)

(73) Assignee: Heidelberg Pharma AG, Heidelberg (DE)

( * ) Notice: Subject to any disclaimer, the term of this patent is extended or adjusted under 35 U.S.C. 154(b) by 93 days.

(21) Appl. No.: 10/549,799

(22) PCT Filed: Mar. 18, 2004

(86) PCT No.: PCT/EP2004/002810

§ 371 (c)(1),
(2), (4) Date: Nov. 21, 2005

(87) PCT Pub. No.: WO2004/083155

PCT Pub. Date: Sep. 30, 2004

(65) Prior Publication Data

US 2006/0293514 A1 Dec. 28, 2006

Related U.S. Application Data

(60) Provisional application No. 60/456,003, filed on Mar. 19, 2003.

(30) Foreign Application Priority Data

Mar. 19, 2003 (EP) .................. 03006059

(51) Int. Cl.
| | |
|---|---|
| A61K 31/70 | (2006.01) |
| C07H 19/19 | (2006.01) |
| C07H 19/20 | (2006.01) |

(52) U.S. Cl. .................. 514/47; 536/26.5; 536/26.6
(58) Field of Classification Search .................. 514/47; 536/26.5, 26.6
See application file for complete search history.

(56) References Cited

U.S. PATENT DOCUMENTS 5,512,671 A 4/1996 Piantadosi et al.

FOREIGN PATENT DOCUMENTS

| EP | 0 219 829 A | 4/1987 |
|---|---|---|
| EP | 0 350 287 A2 | 1/1990 |
| WO | WO 92/03462 A1 | 3/1992 |
| WO | WO 96/15234 A | 5/1996 |

OTHER PUBLICATIONS

Montgomery et al., "Synthesis and Biologic Activity of 2'-Fluoro-2-Halo Derivatives of 9-Beta-D-Arabinofuranosyladenine", Journal of Medicinal Chemistry, vol. 35, No. 2, 1992, pp. 397-401.
Zaitseva et al., "Convergent syntheses and cytostatic properties of 2-chloro-2'-deoxy-2, fluoroadenosine and its N(7)-isomer", Bioorganic & Medicinal Chemistry Letters, vol. 5, No. 24, Dec. 21, 1995, pp. 2999-3002.
Maruyama et al., "Synthesis and anti-HIV activity of 2-substituted 2'-deoxy-2'-fluoroadenosines", Nucleosides and Nucleotides, vol. 13, No. 6-7, 1994, pp. 1219-1230.
Wright et al., "Nucleosides. LX.[1a] Fluorocarbohydrates. XXII.[1b] Synthesis of 2-Dexoy-2-fluoro-D-arabinose . . . ", The Journal of Organic Chemistry, vol. 34, No. 9, Sep. 1969, pp. 2632-2636.
Bosies et al., "Synthesis of Thioether Phosphocholine Analogues", Lipids, vol. 22, No. 11 (1987), pp. 947-951.
Meyer et al., "In Vitro Evaluation f Phosphocholine and Quaternary Ammonium Containing Lipids as Novel Anti-HIV Agents", J. Med. Chem., 1991, vol. 34, pp. 1377-1383.
Hostetler et al., "Synthesis and Antiretroviral Activity of Phospholipid Analogs of Azidothymidine and Other Antiviral Nucleosides", The Journal of Biological Chemistry, vol. 265, Apr. 15, 1990, No. 11, pp. 6112-6117.
Hong et al., "Nucleoside Conjugates. 11. Synthesis and Antitumor Activity of 1-β-D-Arabinofuranosylcytosine and Cytidine Conjugates of Thioether Lipids", J. Med. Chem. 1990, 33, 1380-1386.
Shuto et al., "A Facile Enzymatic Synthesis of 5'-(3-sn-Phosphatidyl)nucleosides and Their Antileukemic Activities", Chem. Pharm. Bull. vol. 36, (1) pp. 209-217, 1988.

*Primary Examiner*—Shaojia Anna Jiang
*Assistant Examiner*—L. E. Crane
(74) *Attorney, Agent, or Firm*—Rothwell, Figg, Ernst & Manbeck, P.C.

(57) ABSTRACT

The subject of the present invention is specific lipidesters of halogenated nucleotides of the following formula (I)

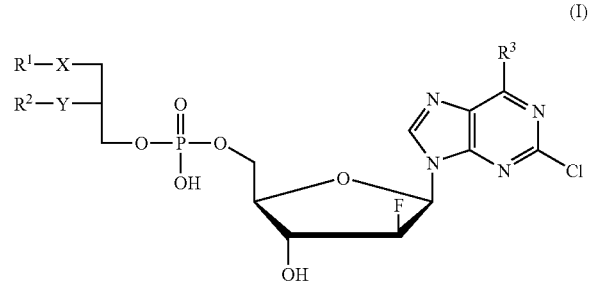

wherein $R^1$, $R^2$, $R^3$, X and Y are defined as described herein and salts thereof, said compounds have anti-cancer properties; pharmaceutical compositions containing the compounds, a method of synthesizing the compounds, and a method of using the compounds for treating malignant tumors.

19 Claims, No Drawings

NUCLEOTIDE LIPID ESTER DERIVATIVES

CROSS REFERENCE TO RELATED APPLICATION

This application is a 35 USC § 371 National Phase Entry Application from PCT/EP2004/002810, filed Mar. 18, 2004, and designating the United States, which claims the benefit of provisional application No. 60/456,003 filed Mar. 19, 2003.

The subject of the present invention are specific lipidesters of nucleotides of the general formula I,

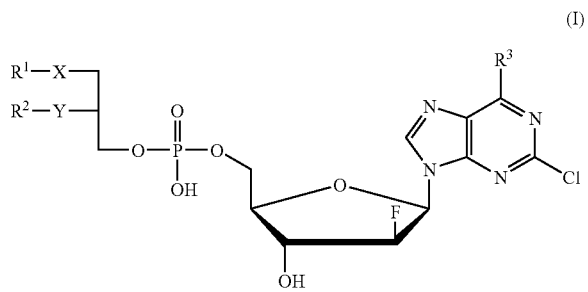

wherein $R^1$ is a straight-chain or branched, saturated or unsaturated alkyl residue having 1-20 carbon atoms, optionally mono- or polysubstituted by halogen, $C_1$-$C_6$ alkoxy, $C_1$-$C_6$ alkylmercapto, $C_1$-$C_6$ alkoxycarbonyl, $C_1$-$C_6$ alkylsulfinyl or $C_1$-$C_6$ alkylsulfonyl groups, $R^2$ is hydrogen, a straight-chain or branched, saturated or unsaturated alkyl chain having 1-20 carbon atoms, optionally mono- or polysubstituted by halogen, $C_1$-$C_6$ alkoxy, $C_1$-$C_6$ alkylmercapto, $C_1$-$C_6$ alkoxycarbonyl or $C_1$-$C_6$ alkylsulfonyl groups, $R^3$ is amino or $OR^4$, wherein $R^4$ is $C_1$-$C_8$ alkyl, x represents a sulfur, a sulfinyl or sulfonyl group, and Y is an oxygen atom, their tautomers and their physiologically acceptable salts of inorganic and organic acids and bases, as well as processes for their preparation and medicaments containing these compounds as active ingredients.

The amino group in the adenine residue of the general formula I can also be protected by well known amino protecting groups.

Since the compounds of the general formula I contain asymmetric carbon atoms, all optically-active forms and racemic mixtures of these compounds are also the subject of the present invention.

J. Biol. Chem. 265, 6112 (1990) and EP-A-0,350,287 describe preparation and use of liponucleotides as anti-viral drugs. Therein, however, only dimyristoylphosphatidyl and dipalmitoylphosphatidyl residues coupled to well known nucleosides such as AZT and DDC are disclosed, including their fatty acid ester structure.

J. Med. Chem. 33, 1380, (1990) describes nucleoside conjugates of thioether lipids with cytidine diphosphate, which have antitumor activity and might find use in oncology.

Chem. Pharm. Bull. 36, 209 (1988) describes 5'-(3-sn-phosphatidyl)nucleosides having antileukemic activity, as well as their enzymatic synthesis from the corresponding nucleosides and phosphocholines in the presence of phospholipase D with transferase activity.

The patent application WO 92/03462 describes thioether lipid conjugates having antiviral activity, particularly for the treatment of HIV infections.

The synthesis of 2-Chloro-9-(2'-deoxy-2'-fluoro-β-Darabinofuranosyl)adenine is described in J. Org. Chem. 34, 2632-2636 (1969), in patent application WO 01/60383, and in U.S. Pat. No. 6,680,382.

The pharmacological activity of 2-Chloro-9-(2'-deoxy-2'-fluoro-β-Darabinofuranosyl)-adenine as inhibitor of DNA replication in comparison to other nucleosides is also described in Hematology 463 (1999).

Other halo arabinoadenosines with anticancer activity are mentioned in the patent applications U.S. Pat. No. 5,384,310 and WO 92/20347.

The antiviral activity of such purine derivatives is shown in EP 0 314 011.

2-Chloro-9-(2'-deoxy-2'-fluoro-β-D-arabinofuranosyl) adenine (Clofarabine) is a well known development product in clinical trials.

The compounds of the present invention of general formula I which incorporate the 2-chloro-9-(2'-deoxy-2'-fluoro-β-D-arabinofuranosyl)adenine chemical structure posses biological activity which distinguish them from the parent nucleoside. In particular, the compounds of the present invention show antitumoral activity and are useful in that, at pharmacological relevant doses, one or more of the toxic side effects of the parent compound is/are ameliorated, and/or the covalently bound lipid moiety improves the bioavailability of the coupled drug substance and thus appears to contribute to enhanced selectivity and effectiveness of the compounds.

The compounds of the present invention have valuable pharmacological properties. In particular, they are suitable for therapy and prophylaxis of malignant tumors including, carcinomas, sarcomas, or leukemias.

Compared to the unconjugated nucleoside derivatives hitherto employed in treatment of malignant tumors, the compounds according to the invention have enhanced potency/efficacy for specific indications or lower toxicity and consequently have a wider therapeutic window. In some embodiments of the present invention, the administration of pharmaceutical compositions comprising these compounds may be conducted continuously over a prolonged period of time. Incidences of withdrawal of the preparation or intermittent administration, which frequently are routine with chemotherapeutic agents due to their undesirable side-effects, may be reduced with the compounds according to this invention as compared to the parent compounds. Further, higher dose levels may be employed due to the amelioration of toxic side effects due to enhanced selectivity for tumor cytotoxicity.

The lipidester compounds of the present invention are also suitable for the treatment of autoimmune disorders, including multiple sclerosis, rheumatoid arthritis, lupus, systemic vasculitis, inflammatory bowel disease, scieroderma and Sjorgen's syndrome.

The lecithin-like structure of the lipid moiety is desirable for the claimed improvements of the compounds of general formula I. The penetration through membranes and resorption barriers is facilitated and the conjugates according to formula I show a depository effect in different tissues.

The formation of lipid conjugates may also facilitate crossing the blood brain barrier due to better diffusion or active transport processes.

Similarly, the compounds of the present invention and their pharmaceutical formulations may be employed in free or fixed combination with other drugs for the treatment and prophylaxis of the diseases mentioned above.

Examples of these further drugs involve agents such as, e.g., mitosis inhibitors such as colchicines, vinblastine, alkylating cytostatic agents such as cyclophosphamide, melphalan, myleran or cis-platin, antimetabolites such as folic acid antagonists (methotrexate) and antagonists of purine and pyrimidine bases (mercaptopurine, 5-fluorouridine, cytarabine), cytostatically active antibiotics such as anthracyclines (e.g., doxorubicin, daunorubicin), hormones such as fosfestrol, tamoxifen, taxanes, e.g. taxol, and other cytostatically/cytotoxically active chemotherapeutic and biologic agents.

Embodiments of the invention also encompass salts of the compounds of the general formula I, including alkali, alkaline earth and ammonium salts of the phosphate group. Examples of the alkali salts include lithium, sodium and potassium salts. Alkaline earth salts include magnesium and calcium and ammonium salts are understood to be those containing the ammonium ion, which may be substituted up to four times by alkyl residues having 1-4 carbon atoms, and/or aryl residues such as benzyl residues. In such cases, the substituents may be the same or different.

The compounds of general formula I may contain basic groups, particularly amino groups, which may be converted to acid addition salts by suitable inorganic or organic acids. To this end, possible as the acids are, in particular: hydrochloric acid, hydrobromic acid, sulphuric acid, phosphoric acid, fumaric acid, succinic acid, tartaric acid, citric acid, lactic acid, maleic acid or methanesulfonic acid.

In general formula I, $R^1$ preferably represents a straight-chain $C_8$-$C_{16}$ alkyl residue which may be further substituted by a $C_1$-$C_6$ alkoxy or a $C_1$-$C_6$ alkylmercapto group. More specifically, $R^1$ represents a nonyl, decyl, undecyl, dodecyl, tridecyl, tetradecyl or pentadecyl residue. Preferably, methoxy, ethoxy, butoxy and hexyloxy groups are possible as substituents of $R^1$ residue. In case $R^1$ is substituted by a $C_1$-$C_6$ alkylmercapto residue, this is understood to be the methylmercapto, ethylmercapto, propylmercapto, butylmercapto and hexylmercapto residue, in particular.

Preferably, $R^2$ represents a straight-chain $C_8$-$C_{15}$ alkyl group which may be further substituted by a $C_1$-$C_6$ alkoxy or a $C_1$-$C_6$ alkylmercapto group. More specifically, $R^2$ represents an octyl, nonyl, decyl, undecyl, dodecyl, tridecyl or tetradecyl group. Preferably, methoxy, ethoxy, propoxy, butoxy and hexyloxy groups are preferable as the $C_1$-$C_6$ alkoxy substituents of $R^2$. In case $R^2$ is substituted by a $C_1$-$C_6$ alkylmercapto residue, this is understood to be the methylmercapto, ethylmercapto, propylmercapto, butylmercapto, pentylmercapto and hexylmercapto residue, in particular.

An example of a preferred lipid moiety is the group

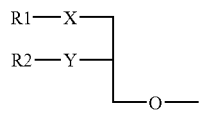

wherein
$R^1$ is $C_{12}H_{25}$
$R^2$ is $C_{10}H_{21}$
X is S, SO or $SO_2$ and
Y is O.

The most preferred compounds are [2-chloro-9-(2'-deoxy-2'-fluoro-β-D-arabinofuranosyl)adenine]-5'-phosphoric acid-(3-dodecylmercapto-2-decyloxy)propyl ester, [2-chloro-9-(2'-deoxy-2'-fluoro-β-D-arabinofuranosyl)adenine]-5'-phosphoric acid-(3-dodecylsulfinyl-2-decyloxy) propyl ester, [2-chloro-9-(2'-deoxy-2'-fluoro-β-D-arabinofuranosyl)adenine]-5'-phosphoric acid-(3-dodecylsulfonyl-2-decyloxy)propyl ester as well as [2-chloro-9-(2'-fluoro-β-D-arabinofuranosyl)-6-methoxy-9H-purine]-5'-phosphoric acid-(3-dodecylmercapto-2-decyloxy)propyl ester, [2-chloro-9-(2'-fluoro-β-D-arabinofuranosyl)-6-methoxy-9H-purine]-5'-phosphoric acid-(3-dodecylsulfinyl-2-decyloxy)propyl ester and [2-chloro-9-(2'-fluoro-β-D-arabinofuranosyl)-6-methoxy-9H-purine]-5'-phosphoric acid-(3-dodecylsulfonyl-2-decyloxy)propyl ester.

The compounds of the general formula I may be prepared by
1. reacting a compound of general formula II, or a salt form thereof,

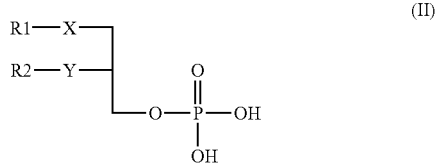

wherein $R^1$, $R^2$, X and Y have the meaning as indicated, with a compound of general formula III

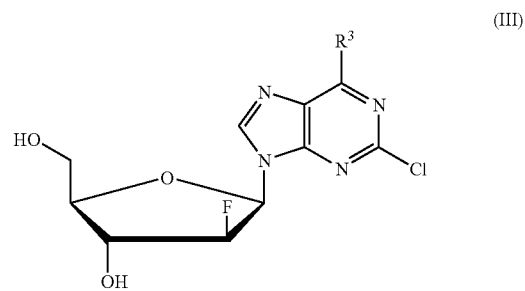

wherein $R^3$ is amino or $OR^4$, wherein $R^4$ is $C_1$-$C_8$ alkyl and the 3'-hydroxy group may optionally be protected by an oxygen protecting group familiar to the artisan, and the compound of formula II may be activated in the presence of an appropriate acid chloride, such as 2,4,6-triisopropylbenzene-sulfonic chloride, and a tertiary nitrogen base, e.g., pyridine or lutidine, in an inert solvent, such as toluene, or immediately in anhydrous pyridine, and optionally, subsequent to hydrolysis, removing the oxygen protecting groups according to procedures conventional in nucleoside chemistry, and, when $R^3$ is to be amino in compounds of formula I optionally conversion of the $OR^4$ group at the purine 6 position to an amino group, or reacting a lipidalcohol (corresponding to formula II) with a nucleoside-5'-monophosphate (corresponding to formula III) in the same manner as mentioned above, or 2. reacting a compound of general formula IV,

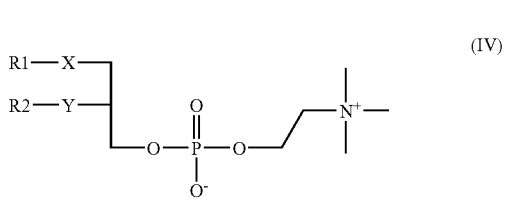

wherein $R^1$, $R^2$, X and Y have the above-mentioned meaning, with a compound of general formula III, wherein $R^3$ is amino or $OR^4$, wherein $R^4$ is $C_1$-$C_8$ alkyl and the 3'-hydroxy group may optionally be protected by an oxygen protecting group familiar to the artisan, in the presence of phospholipase D from Streptomyces in an inert solvent, such as chloroform, in the presence of a suitable buffer, and optionally, subsequent to reaction, removing the oxygen protecting groups according to procedures conventional in nucleoside chemistry and, when $R^3$ is to be amino in compounds of formula I optionally conversion of the $OR^4$ group at the purine 6 position to an amino group.

The preparation of the compounds of the general formula II and IV is performed in analogy to Lipids 22, 947 (1987) and J. Med. Chem. 34, 1377 (1991). Compounds of formula III are prepared in analogy to J. Org. Chem. 34, 2632-2636 (1969), J. Med. Chem. 35, 397-401 (1992) or WO 01/60383 if $R^3$ is an amino group or if $R^3=OR^4$ in two steps. The first step comprises the preparation of 2,6-dichloro-9-(3', 5'-O-dibenzoyl-2'-deoxy-2'-fluoro-β-D-arabinofuranosyl)-9H-purine by reacting 2,6-dichloropurine with a blocked 2-deoxy-2-fluoro-β-D-arabinofuranosyl halide in a suitable solvent in the presence of a hindered potassium base, preferably potassium t-butoxide or potassium t-amylate. Suitable blocking groups include benzoyl and acetyl. Suitable halides include bromo and chloro. Suitable inert solvents include, but are not limited to, t-butyl alcohol, acetonitrile, dichloromethane, dichloroethane, t-amyl alcohol, tetrahydrofuran or mixtures thereof. A preferred solvent comprises a mixture of acetonitrile, t-butanol and 1,2-dichloroethane. Calcium hydride may be optionally added to the reaction mixture. The second step comprises subjecting the 2,6-dichloro purine nucleoside derivative to conditions that provide for deprotection and an aromatic nucleophilic substitution reaction, e.g., sodium hydroxide and $C_1$-$C_8$ alcohol or sodium $C_1$-$C_8$ alkoxide in the corresponding $C_1$-$C_8$ alcohol (e.g., methanol with sodium methoxide, ethanol with sodium ethoxide, etc.) or other suitable nonalcoholic solvent, to provide the desired $C_1$-$C_8$ 6-alkoxy purine nuceloside compound of formula III.

The compounds of formula I wherein X=sulfinyl or sulfonyl can be prepared by oxidation of the corresponding compounds of formular I wherein X=sulfur with, e.g., $H_2O_2$/acetic acid or by using appropriate starting compounds of formular II or IV.

Other compounds of the present invention are diphosphates of formula V wherein n=2 and $R^1$, $R^2$, $R^3$, X and Y have the same meaning as in formula I.

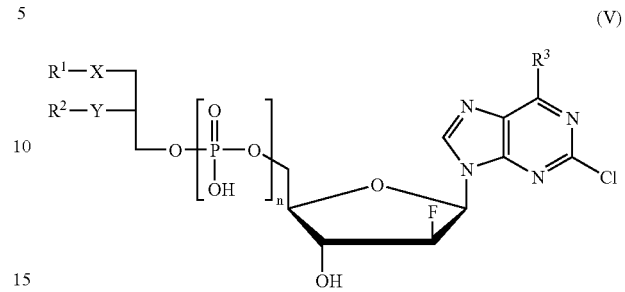

They may be prepared by reacting a (ipidphosphate (corresponding to formula II) with a nucleoside-5'-monophosphate (prepared from nucleosides corresponding to formula III).

The lipid phosphate may be activated before by a method familiar to the artisan.

Salts of compounds of general formula I are prepared by reacting the free acid with alkali or alkaline earth hydroxides, alcoholates or acetates.

The "enantiomers" in the lipid parts of the compounds of formula I may be prepared by separation via diastereomeric salts or by enantioselective synthesis of the lipid residues starting with optically active $C_3$-precursors of formula II.

The drugs containing compounds of formula I for the treatment of cancer may be administered in liquid or solid forms on the oral or parenteral route. Common application forms are possible, such as tablets, capsules, coated tablets, syrups, solutions, or suspensions.

Preferably, water is used as the injection medium, containing additives such as stabilizers, solubilizers and buffers as are common with injection solutions. Such additives are, e.g., tartrate and citrate buffers, ethanol, complexing agents such as ethylenediaminetetraacetic acid and its non-toxic salts, high-molecular polymers such as liquid polyethylene oxide for viscosity control. Liquid vehicles for injection solution need to be sterile and are filled in ampoules, preferably.

Solid carriers are, for example, starch, lactose, mannitol, methylcellulose, talc, highly dispersed silicic acids, higher-molecular fatty acids such as stearic acid, gelatine, agar-agar, calcium phosphate, magnesium stearate, animal and plant fats, solid high-molecular polymers such as polyethylene glycol, etc. If desired, formulations suitable for oral application may include flavorings or sweeteners.

The dosage may depend on various factors such as mode of application, species, age, or individual condition.

The compounds according to the invention may suitably be administered orally or intravenously (i.v.) in amounts in the range of 0.1-100 mg, preferably in the range of 0.2-80 mg per kg of body weight and per day. In some dosage regimens, the daily dose is divided into 2-5 applications, with tablets having an active ingredient content in the range of 0.5-500 mg being administered with each application.

Similarly, the tablets may have sustained release, reducing the number of applications, e.g., to 1-3 per day. The active ingredient content of sustained-release tablets may be in the range of 2-1000 mg. The active ingredient may also be administered by i.v. bolus injection or continuous infusion, where amounts in the range of 5-1000 mg per day are normally sufficient.

In addition to the compounds mentioned in the examples, the following compounds of formula I and their pharmacologically acceptable salts further exemplify compounds of the present invention:

1. [2-Chloro-9-(2'-deoxy-2'-fluoro-β-D-arabinofuranosyl)adenine]-5'-phosphoric acid-(3-dodecylmercapto-2-decyloxy)propyl ester
2. [2-Chloro-9-(2'-deoxy-2'-fluoro-β-Darabinofuranosyl)adenine]-5'-phosphoric acid-(3-dodecylsulfinyl-2-decyloxy)propyl ester
3. [2-Chloro-9-(2'-deoxy-2'-fluoro-β-Darabinofuranosyl)adenine]-5'-phosphoric acid-(3-dodecylsulfonyl-2-decyloxy)propyl ester
4. [2-Chloro-9-(2'-deoxy-2'-fluoro-β-Darabinofuranosyl)adenine]-5'-phosphoric acid-(3-undecylmercapto-2-decyloxy)propyl ester
5. [2-Chloro-9-(2'-deoxy-2'-fluoro-β-Darabinofuranosyl)adenine]-5'-phosphoric acid-(3-undecylmercapto-2-undecyloxy)propyl ester
6. [2-Chloro-9-(2'-deoxy-2'-fluoro-β-Darabinofuranosyl)adenine]-5'-phosphoric acid-(3-decylmercapto-2-dodecyloxy)propyl ester
7. [2-Chloro-9-(2'-deoxy-2'-fluoro-β-D-arabinofuranosyl)adenine]-5'-phosphoric acid-(3-dodecylmercapto-2-dodecyloxy)propyl ester
8. [2-Chloro-9-(2'-deoxy-2'-fluoro-β-Darabinofuranosyl)adenine]-5'-phosphoric acid-(3-decylmercapto-2-decyloxy)propyl ester
9. [2-Chloro-9-(2'-deoxy-2'-fluoro-β-D-arabinofuranosyl)adenine]-5'-phosphoric acid-(3-undecylsulfinyl-2-decyloxy)propyl ester
10. [2-Chloro-9-(2'-deoxy-2'-fluoro-β-Darabinofuranosyl)adenine]-5'-phosphoric acid-(3-undecylsulfonyl-2-decyloxy)propyl ester
11. [2-Chloro-9-(2'-deoxy-2'-fluoro-β-Darabinofuranosyl)adenine]-5'-phosphoric acid-(3-undecylsulfinyl-2-undecyloxy)propyl ester
12. [2-Chloro-9-(2'-deoxy-2'-fluoro-β-Darabinofuranosyl) adenine]-5'-phosphoric acid-(3-undecylsulfonyl-2-undecyloxy)propyl ester
13. [2-Chloro-9-(2'-deoxy-2'-fluoro-β-Darabinofuranosyl)adenine]-5'-phosphoric acid-(3-tridecylmercapto-2-undecyloxy)propyl ester
14. [2-Chloro-9-(2'-deoxy-2'-fluoro-β-D-arabinofuranosyl)adenine]-5'-phosphoric acid-(3-tridecylmercapto-2-decyloxy)propyl ester
15. [2-Chloro-9-(2'-deoxy-2'-fluoro-β-Darabinofuranosyl)adenine]-5'-phosphoric acid-(3-tridecylsulfinyl-2-decyloxy)propyl ester Further, the present invention encompasses the analogs of the foregoing exemplified compounds wherein the substituent at the purine 6-position is $C_1$-$C_8$ alkoxy, preferably methoxy. Such compounds have also excellent pharmaceutical properties and in addition are useful as intermediates in the preparation of said forgoing exemplified compounds.

EXAMPLE 1

Preparation of 2-chloro-6-methoxy-9-(2'-deoxy-2'-fluoro-β-D-arabinofuranosyl)-9H-purine The first step was to prepare 2,6-dichloro-9-α-D-(3', 5'-O-dibenzoyl-2'-deoxy-2'-fluoro-β-Darabinofuranosyl)-9H-purine according to the following scheme:

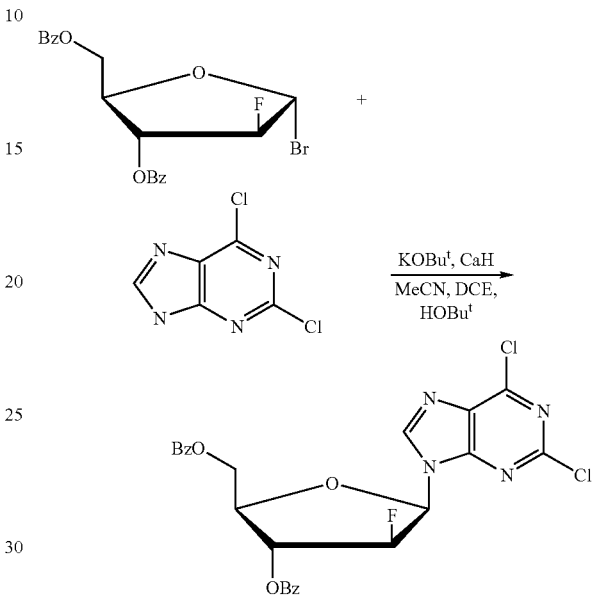

A 1000 mL flask was charged with 2,6-dichloropurine (12.65 g, 66.9 mmol), calcium hydride (2.43 g, 57.7 mmol) and acetonitrile (150 mL) and stirring was started. A solution of potassium tert-butoxide (60.6 mL, 60.6 mmol, 1.0 M in tert-butanol) was added over 5 min to give a viscous but stirrable suspension. A solution of 3,5-O-dibenzoyl-2-deoxy-2-fluoro-α-D-arabinofuranosyl bromide (26.88 g, 63.5 mmol) in 1,2-dichloroethane (200 mL) was added over 45 min at ambient temperature. After addition was complete, the mixture was stirred at ambient temperature for 16 hours. The mixture was filtered through Celite and the flask and solids were washed with acetonitrile (100 mL). The volatiles were removed by rotary evaporation to give a yellow gum (38.1 g). Ethylacetate (100 mL) was added, the pH was checked, and was found to be 8. Acetic acid (0.5 mL) was added, the pH was rechecked, and was found to be 4. The cloudy solution was filtered through Whatman 541 filter paper. The flask and filter were washed with ethylacetate (100 mL). No clarification of the solution was observed. The organic layer was washed with water (100 mL) then brine (100 mL). The organic layer was dried ($MgSO_4$) and reduced by rotary evaporation then high vacuum pump to give a white foam (34.0 g). The crude material was purified by column chromatography (silica gel 60, 230-400 mesh, 14 cm diameter, 14.5 cm height, 2232 mL). A gradient elution of hexanes/ethylacetate was used and the fractions containing the purest product were reduced by rotary evaporation, slurried twice in methanol, filtered and washed with methanol to give a white solid (13.4 g, 92.6% AUC). Less pure fractions were combined, reduced by rotary evaporation and repurified by column chromatography to give a white solid (3.85 g, 94.7% AUC). Total recovery was 17.3 g (56%). A portion was reslurried in methanol for characterization (97.9% AUC). mp=157-159° C. $^1$H NMR (DMSO-$d_6$) δ8.84 (d, 1H, J=2.82 Hz, $H_8$), 8.14-8.00 (m, 4H, Bz), 7.76-7.50 (m, 6H, Bz), 6.81 (dd, 1H, J=18.2, 3.9 Hz, $H_{1'}$), 5.95 (m, 2H, $H_{3'}$), 5.91 (dm, 1H, J=75.4 Hz, $H_{2'}$), 4.84-4.79 (m, 3H, $H_4$ and $H_{5'}$). $^{13}$C NMR (DMSO-$d_6$) 165.4, 164.8, 152.7, 151.6, 150.3, 146.7 (d, $J_{(CF)}$=4 Hz), 133.9, 133.4, 130.3, 129.6, 129.2, 128.7, 128.6, 128.5, 92.9 (d, $J_{(CF)}$=192 Hz), 82.8 (d, $J_{(CF)}$=16 Hz), 78.9, 76.2 (d, $J_{(CF)}$=28 Hz), 63.7 ppm. $^{19}$F NMR (DMSO-$d_6$)-197.6 (dt, J=50, 19 Hz) ppm. IR (KBr) 3431, 3139, 3063, 2966, 1726, 1596, 1272, 1091, 714 cm$^{-1}$. UV (H$_2$0/MeCN) λmax$_1$ 214 nm (0.94AU), λmax$_2$ 231 nm (0.90AU), λmax$_3$ 273 nm (0.37AU). Mass spec.(electrospray, positive) m/e [M+H]$^+$=531. Elemental analysis calculated for $C_{24}H_{17}Cl_2FN_4O_5$: C, 54.25; H, 3.22; Cl, 13.35:, F, 3.58; N, 10.54. Found: C, 54.19; H, 3.11; Cl, 13.20; F, 3.49; N, 10.52.

The second step was to prepare 2-chloro-6-methoxy-9-(2'-deoxy-2'-fluoro-β-D-arabinofuranosyl)-9H-purine according to the following scheme:

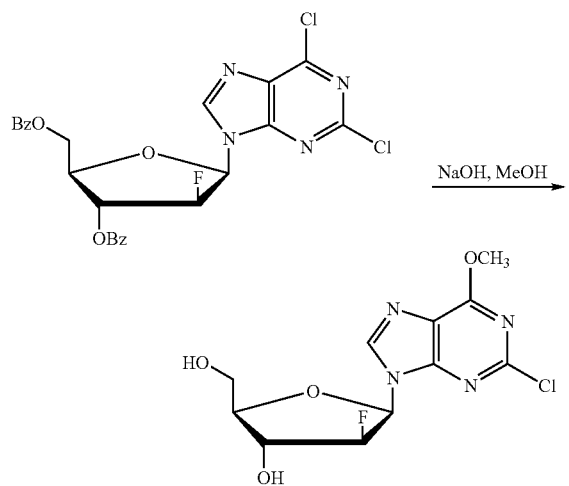

A 500 mL flask was charged with protected 2,6-dichloro-9-α-D-(3', 5'-O-dibenzoyl-2'-deoxy-2'-fluoro-β-D-arabinofuranosyl)-9H-purine (13.33g, 25.1 mmol) and methanol (300 mL). The pH was adjusted to 9.5 with a solution of NaOH (2 mL, 1.0 N in H$_2$O). The suspension was stirred at ambient temperature for 16.5 hours. The pH was checked and was found to be 5.5. More NaOH solution (11.3 mL) was added (pH=11) and the mixture was stirred at ambient temperature for 1.5 hours. The pH was checked and found to be 6. TLC (10% EtOH/90% CH$_2$Cl$_2$, UV$_{254}$) showed 3 spots at R$_f$ 0.28, 0.72 and 0.88. More NaOH solution (13.3 mL) was added (pH=11). After stirring for 5 min at ambient temperature, the reaction mixture became a clear colorless solution and after stirring for an additional 2.5 hours, the reaction was judged complete by TLC. Acetic acid (0.8 mL) was added to neutralize the base (pH=5). Rotary evaporation yielded a biphasic residue. Isopropyl alcohol (100 mL) was added to give a white suspension. Water was removed via azeotropic rotary evaporation. This process was repeated twice more with isopropyl alcohol (100 mL). Rotary evaporation was stopped with approximately 50 mL remaining in the flask and the suspension was filtered and the flask and filtercake were washed with the filtrate, then isopropyl alcohol (10 mL). The solid was dried (50° C., 27 torr, 16.5 h). Weight of the solid was 5.58 g (92.4% AUC). The filtrate was reduced by rotary evaporation and high vacuum pump. Weight of the residue was 6.79 g (70.9% AUC). Both the solid and the residue were purified separately by column chromatography (silica gel 60, 230-400 mesh, 10% ethanol, 90% dicholoromethane). Weight of the purified material from the crude solid was 4.62 g (95.5% AUC). Weight of the purified material form the residue was 1.69 g (98.1% AUC). Total recovery was 6.31 g (79%). mp=197-201 ° C. $^1$H NMR (DMSO-$d_6$) δ 8.59 (d, 1H, J =1.9 Hz, $H_8$), 6.47 (dd, 1H, J=12.8, 4.9 Hz, $H_{1'}$), 6.02 (d, 1H, J=5.4 Hz, 3'-OH), 5.31 (dt, 1H, J =52.5,4.5 Hz, $H_{2'}$), 5.15 (t, 1H, J=5.7 Hz, 5'-OH), 4.47,ddd, 1H, J=19.1, 9.9, 5.3 Hz, $H_{3'}$), 4.13 (s, 1H, MeO), 3.90 (dd, 1H, J=9.7, 4.7 Hz, $H_{4'}$), 3.75-3.64 (m, 2H, $H_{5'}$). $^{13}$C NMR (DMSO-$d_6$) 160.9, 152.6, 151.8, 143.0, 119.7, 95.3 (d, $J_{(CF)}$=193 Hz), 83.6 (d, $J_{(CF)}$=7 Hz), 81.8 (d, $J_{(CF)}$=17 Hz), 72.3 (d, $J_{(CF)}$=23 Hz), 60.2, 55.1 ppm. $^{19}$F NMR (DMSO-$d_6$)–199.1(ddd, J=53,19,13 Hz) ppm. IR (KBr) 3438, 3235, 3113, 2916, 1599, 1471, 1389, 1320, 1238, 1045, 925, 691 cm$^{-1}$. UV (H$_2$O/MeCN) λmax$_1$, 210 nm (1.00AU), λmax$_2$ 257 nm (0.67AU). Mass spec.(electrospray, positive) m/e [M+H]$^+$=319. Anal. Calcd for $C_{11}H_{12}ClFN_4O_4$: C, 41.46; H, 3.80; Cl, 11.12:, F, 5.96; N, 17.58. Found: C, 41.70; H, 3.36; Cl, 11.12; F, 5.75; N, 17.54.

EXAMPLE 2

Preparation of [2-Chloro-9-(2'-deoxy-2'fluoro-β-D-arabinofuranosyl)adenine]-5'-phosphoric acid-(3-dodecylmercapto-2-decyloxy)propyl ester The first step is the preparation of [2-chloro-9-(2'-fluoro-β-D-arabinofuranosyl)-6-methoxy-9H-purine ]-5'phosphoric acid-(3-dodecylmercapto-2-decloxy)propyl ester as follows:

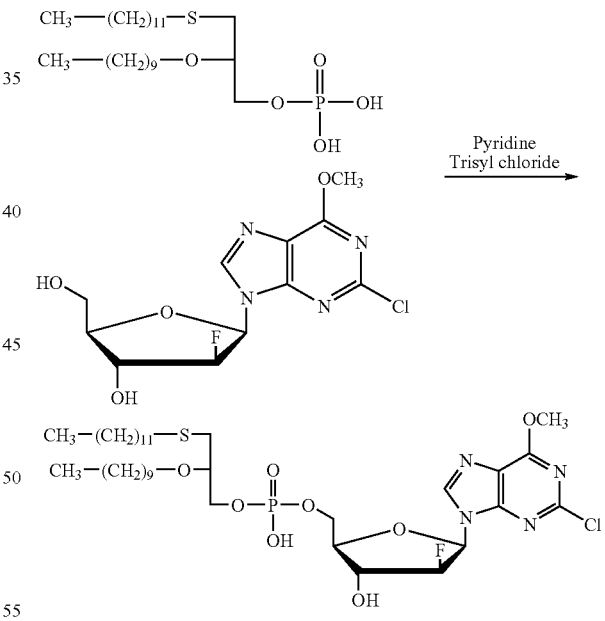

3.12 g of phosphoric acid-(3-dodecylmercapto-2-decyloxy)propyl ester was treated twice with 60 ml of anhydrous pyridine and concentrated by evaporation. The residue was dissolved in 60 ml of anhydrous pyridine at room temperature, treated with 3,80 g of 2,4,6-triisopropylbenzenesulfonyl chloride (trisyl choride) under nitrogen and stirred at 20° C. for 2 hours. Then 2,00 g of 2-chloro-9-(2'-deoxy-2'-fluoro-β-D-arabinofuranosyl)-6-methoxy-9H-purine was added at once, and the charge was stirred under nitrogen for 16 hours. Hydrolysis was performed by adding 10 ml of water, the mixture was stirred for another 0.5 hour at room temperature, freed from solvent under vacuum, and stripped twice using 20 ml of toluene. The residue was stirred in t-butylmethylether (160 ml) at 40° C. for 0.5 h. After cooling to room temperature, the pyridinium sulfonate salt was filtered off. The filtrate was washed twice with 40 ml 2N hydrochloric acid and evaporated to dryness. The remaining syrupy 7.38 g material is used in the next step without further purification.

A sample of the above raw material was purified by column chromatography on Lichrospher 60 RPSelect B with methanovaqueous 40 mM sodium acetate 90:10 as the eluent. The product containing fractions were evaporated and the residue was distributed between 50 ml of tert.-butylmethylether and 10 ml of 2N hydrochloric acid. The organic layer was evaporated and the residue dissolved in a mixture of 5 ml of toluene and of 5 ml of methanol. The pH was adjusted to pH 7 by addition of sodium methanolate. The solvent was stripped off and the residue was dried in vacuum. The sodium salt of [2-chloro-9-(2'-fluoro-β-D-arabinofuranosyl)-6-methoxy-9H-purine]-5'-phosphoric acid-(3-dodecylmercapto-2-decyloxy)propyl ester was received as an amorphous solid that melts as 65-75° C. with a specific rotation of $[\alpha]_{20}^{Hg436} = +31.9$ (c =1.0 in methanol).

$^1$H NMR (300 MHz, DMSO-d$_6$): 8.5 (s, 1H, H$_8$), 6.6, (s (br), 1H, 3'-OH), 6.4 (dd, 1 H, H$_{1'}$), 5.3 (dt, 1H, H$_{2'}$), 4.4, (dt, 1H, H$_{3'}$), 4.1 (s, 3H, OCH$_3$), 3.9-4.0, (m, 3H, H$_{4'}$, POCH$_2$), 3.6, (m, 1H, H$_{5'a}$), 3.6 (m, 1H, H$_{5'b}$), 3.3-3.4 (m, 3H, >CHOCH$_2$—), 2.5-2.6(m, 4H, CH$_2$SCH$_2$), 1.1-1.5 (m, 36H, —(CH$_2$)$_9$—, —(CH$_2$)$_7$—), 0.8 (m, 6H, CH$_2$—CH$_3$); $^3J_{1'\text{-}H,2'\text{-}H} \approx {}^3J_{2'\text{-}H,3'\text{-}H} \approx {}^3J_{3'\text{-}H,4'\text{-}H} \approx 4.7$ Hz, $^3J_{1'\text{-}H,F} = 12.1$ Hz, $^2J_{2'\text{-}H,F} = 52.8$ Hz, $^3J_{3'\text{-}H,F} = 19.0$ Hz.

$^{13}$C-NMR (75,0 MHz, DMSO-d$_6$): 160.8, 152.6, 151.7(C-2,C-4,C-6), 142.9, (C-8), 119.6, (C-5), 94.9, (C-2'), 82.2, (C-4'), 81.6, (C-1'), 78.7,(O—CH<),73.7, (C-3'), 69.1, (CH$_2$—CH$_2$O—CH<), 64.8, (C-5'), 63.4, (5'-O—P(O)$_2$OCH$_2$), 55.0, (6-CH$_3$), 32.1, 32.3, (—CH$_2$SCH$_2$—), 20.0-31.2 (—(CH$_2$)$_9$—, —(CH$_2$)$_7$—), 13.9, 2×CH$_3$) $^{31}$P NMR (121,5 MHz, DMSO-d$_6$): –0.46 ppm. UV (methanol)λ$_{max1}$ 205.3 nm, λ$_{max2}$ 255.9 nm, mass spec. (FAB$^-$): m/z=795 [M–Na$^+$], The second step was subjecting the crude [2-chloro-9-(2'-fluoro-β-D-arabinofuranosyl)-6-methoxy-9H-purine]-5'-phosphoric acid-(3-dodecylmercapto-2-decyloxy)propyl ester to aminolysis to provide [2-Chloro-9-(2'-deoxy-2'-fluoro-β-Darabinofuranosyl)adenine]-5'-phosphoric acid-(3-dodecylmercapto-2-decyloxy)propyl ester:

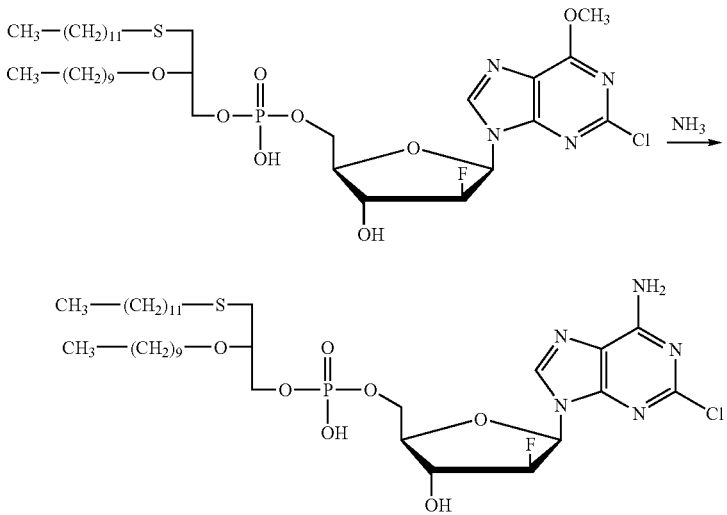

The aminolysis step was carried out in a stainless steel reactor at 80° C. The above mentioned crude material (7,38 g) was dissolved in 30 ml 7 M NH$_3$ in ethanol (saturated at –5° C.). No [2-chloro-9-(2'-fluoro-β-D-arabinofuranosyl)-6-methoxy-9H-purine]-5'-phosphoric acid-(3-dodecylmercapto-2-decyloxy)propyl ester methoxyderivate reactant could be detected after 20 h heating. The product was purified by column chromatography on Lichrospher 60 RPSelect B with methanol/aqueous 40 mM sodium acetate 85:15 as the eluent. The product containing fractions are evaporated. The residue is distributed between 100 ml of tert.-butylmethylether and 50 ml of 2 N hydrochloric acid. The organic layer is evaporated, the residue is dissolved in a mixture of 30 ml of methanol and the pH is adjusted to pH 7 by addition of sodium methanolate (30% in methanol). The solvent is stripped of and the residual sodium salt is dried in vacuum. The product (2.90 g) is achieved in 57% overall yield based on conversion from 2-chloro-9-(2'-deoxy-2'-fluoro-β-D-arabinofuranosyl)-6-methoxy-9H-purine. Purity as determined by HPLC was 93.6 area-percent. Melting point: 130-131° C. MS (FAB$^-$): m/z=780 [M–Na+], UV (methanol) λmax 263.4 nm.

$^1$H NMR (300 MHz, DMSO-d$_6$): 8.2 (s, 1H, H$_8$), 7.7, (s (br), 1H, NH$_2$), 6,5, (s (br), 1H, 3'-OH), 6.2 (dd, 1H, H$_{1'}$), 5.2 (dt, 1H, H$_{2'}$), 4.4, (dt, 1H, Hz, H$_{3'}$), 3.8-4.0, (m 3H, H$_{4'}$, POCH$_2$), 3.6, (m, 1H, –H$_{5a'}$), 3.6 (m, 1H, H$_{5'b}$), 3.3-3.5 (m, 3H, >CHOCH$_2$—), 2.5-2.7 (m, 4H, CH$_2$SCH$_2$), 1.1-1.4(m, 36H, —(CH$_2$)$_9$—, —(CH$_2$)$_7$—), 0.8(m, 6H, CH$_2$—CH$_3$); $^3J_{1'\text{-}H,2'\text{-}H} \approx {}^3J_{2'\text{-}H,3'\text{-}H} \approx {}^3J_{3'\text{-}H,4'\text{-}H} \approx 4.2$ Hz, $^3J_{1'\text{-}H,F} = 14.1$ Hz, $^2J_{2'\text{-}H,F} = 54$ Hz, $^3J_{3'\text{-}H,F} = 19.0$ Hz. $^{13}$C NMR (75,0 MHz, DMSO-d6): 156.8, 153.3, 150.1 (C-2,C4,C-6), 139.8, (C-8), 117.3, (C-5), 95.0,(C-2'), 81.8,(C4'), 81.2, (C-1'), 78.8, (O—CH<), 72.9, (C-3'), 69.1, (CH$_2$—CH$_2$O—CH<), 64.8, (C-5'), 64.4, (5'-O—P(O)$_2$OCH$_2$), 32.1, 31.3, (—CH$_2$SCH$_2$—), 22.1-29.7 (—(CH$_2$)$_9$—, —(CH$_2$)$_7$—), 13.9, (2×CH$_3$) $^{31}$P NMR (121,5 MHz, DMSO-d$_6$): –0.48 ppm $^{19}$F NMR (282 MHz, DMSO-d$_6$): –198.7 ppm.

EXAMPLE 3

Preparation of [2-Chloro-9-(2'-deoxy-2'-fluoro-β-D-arabinofuranosyl)-adenine]-5'-phosphoric acid-(3-dodecylmercapto-2-decyloxy)propyl ester from 2-Chloro-9-(2'-deoxy-2'-fluoro arabinofuranosyl) adenine 0.91 g of phosphoric acid-(3-dodecylmercapto-2-decyloxy)propyl ester are treated twice with 20 ml of anhydrous pyridine and concentrated by evaporation. The residue is dissolved in 20 ml of anhydrous pyridine at room temperature, treated with 1.07 g of 2,4,6-triisopropylbenzenesulfonic chloride under nitrogen and stirred at 25° C. for 0.5 hours. Then 0.5 g of 2-Chloro-9-(2'-deoxy-2'-fluoro arabinofuranosyl)adenine are added at once, and the charge is allowed to stand under nitrogen for 20 hours. Hydrolysis is performed by adding 5 ml of water, the mixture is stirred for another 0.5 hour at room temperature, freed from solvent under vacuum, and stripped twice using 50 ml of toluene. The residue is purified by column chromatography on Lichrospher 60 RPS-elect B with methanol/aqueous 40 mM sodium acetate 88:12 as the eluent. The product containing fractions are evaporated. The residue is distributed between 50 ml of tert.-butyl-methylether and 10 ml of 2N hydrochloric acid. The organic layer is evaporated. The residue is dissolved in a mixture of 5 ml of toluene and of 5 ml of methanol. The pH is adjusted to pH 7 by addition of sodium methanolate. The solvent is stripped of and the residue is dried in vacuum.

The yield is 0.82 g (62%) white powder.

The phosphoric acid-(3-dodecylmercapto-2-decyloxy) propyl ester is prepared as described in WO 92/03462.

EXAMPLE 4

Preparation of [2-chloro-9-(2'-deoxy-2'-fluoro-β-D-arabinofuranosyl)adenine]-5'-diphosphoric acid, (3-dodecylmercapto-2-dodecyloxy)propyl ester The first step is the preparation of 2-chloro-6-methoxy-9-(2'-deoxy-2'-fluoro-5'-O-phosphate-β-D-arabinofuranosyl)-9H-purine from 2-chloro-6-methoxy-9-(2'-deoxy-2'-fluoro-β-D-arabinofuranosyl)-9H-purine:

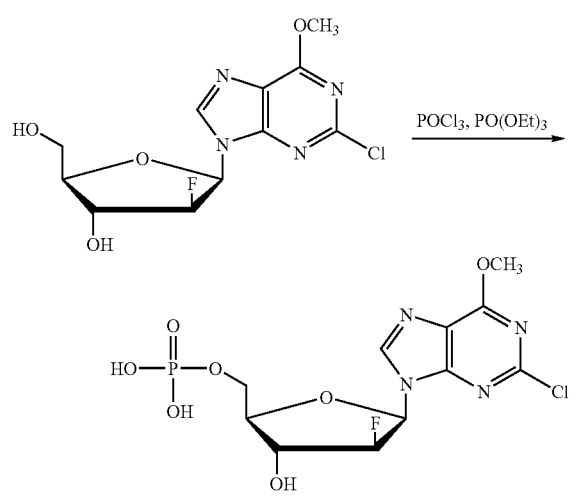

A flask is charged with 2-chloro-6-methoxy-9-(2'-deoxy-2'-fluoro-β-D-arabinofuranosyl)purine and triethylphosphate (e.g., 2.3 mL/mmole nucleoside) under nitrogen. The resulting mixture is cooled (e.g., −25° C.) and then POCl₃ (e.g., 3 eq.) is charged. Upon warming to ambient temperature, the mixture is stirred (e.g., 3 h). Ice (e.g., 1.4 g/mmole nucleoside) and water (e.g., 8.7 mL/mole nucleoside) is then added with stirring and the mixture transferred to a separatory funnel. MTBE (e.g., 4.4 mL/mole nucleoside) is added and the phases separated after agitation. The organic phase is washed twice with water (e.g., 8.7 mL/mmole nucleoside). The combined aqueous extracts is acidified to approximately pH 2 with NaOH (e.g., 50% aq.) and then stirred with activated charcoal (e.g., 5.7 g/mmole nucleoside) for a suitable time (e.g., 2 h). The mixture is filtered and the filtrate discarded. The charcoal is stirred with a mixture of MeOH (e.g., 4.4 mL/mmole nucleoside), ammonium hydroxide (conc.) (e.g. 0.44 mL/mmole nucleoside) and water (e.g., 3.9 mL/mmole nucleoside) for a suitable time (e.g., 30 min) and filtered. The procedure is repeated (e.g., 5 times) and the filtrates are combined. Evaporation of the combined filtrates provides crude 2-chloro-6-methoxy-9-(2'-deoxy-2'-fluoro-5'-O-phosphate-β,-D-arabinofuranosyl)-9H-purine. This is dissolved in water (e.g., 8.7 mL/mmole nucleoside) and treated with Dowex 50WX8-100 (e.g., 4 g/mmole nucleoside) cationic resin with stirring for a suitable time (e.g., 30 min). The mixture is filtered and the resin stirred with water (e.g., 9 mL/mmole nucleoside) and filtered. The resin is extracted with water (e.g. four times) and the combined water filtrates are evaporated to afford 2-chloro-6-methoxy-9-(2'-deoxy-2'-fluoro-β-D-arabinofuranosyl)-9H-purine (e.g., in 30-100% yield).

The second step is the aminolysis of 2-chloro-6-methoxy-9-(2'-deoxy-2'-fluoro-β-D-arabinofuranosyl)-9H-purine to afford 2-chloro-9-(2'-deoxy-2'-fluoro-5'-O-phosphate-β,-D-arabinofuranosyl)adenine:

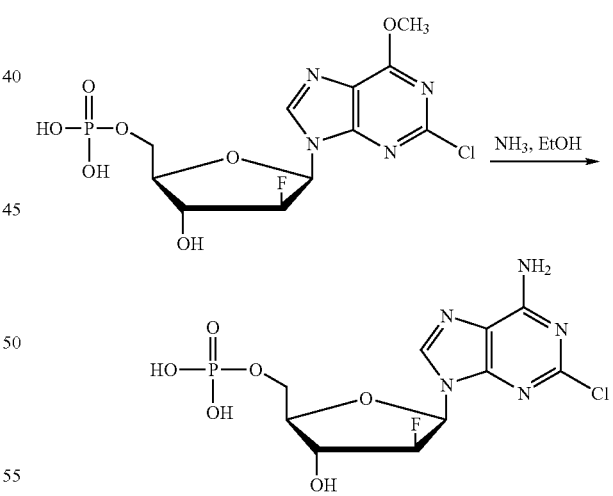

2-Chloro-6-methoxy-9-(2'-deoxy-2'-fluoro-β-D-arabinofuranosyl)purine is dissolved in anhydrous ethanol in a pressure vessel and cooled under nitrogen (e.g., −5° C.). Ammonia is introduced into the solution until a saturated solution is achieved. The system is then heated (e.g., to 80° C.) for a suitable time (e.g., >20 h). The progress of the reaction is monitored by sampling and HPLC analysis. Upon completion, the solvent is evaporated to afford crude 2-chloro-9-(2'-deoxy-2'-fluoro-5'-O-phosphate-β-D-arabinofuranosyl)adenine.

The third step is the production of (2-chloro-9-(2'-deoxy-2'-fluoro-β-D-arabinofuranosyl)adenine-5'-diphosphoric acid, (3-dodecylmercapto-2-dodecyloxy)propyl ester by reacting the morpholidate of phosphoric acid mono-(3-dodecylmercapto-2-decyloxy)-1-propyl ester with 2-chloro-9-(2'-deoxy-2'-fluoro-5'-O-phosphate-β-D-arabinofuranosyl)adenine:

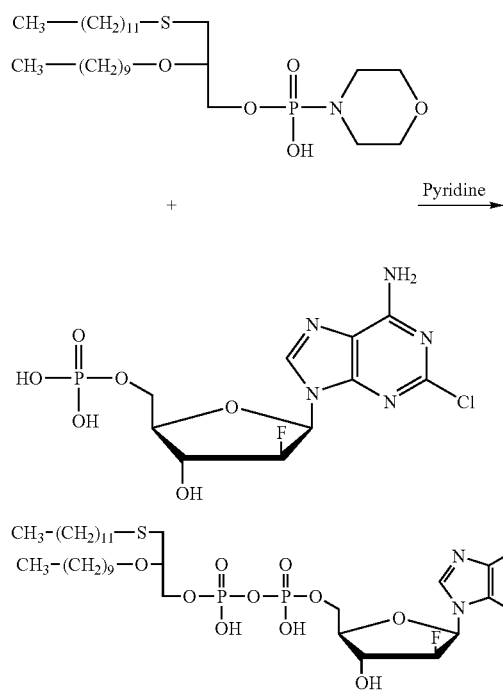

The morpholidate of phosphoric acid mono(3-dodecylmercapto-2-decyloxy)-1-propyl ester is prepared by analogy to Bioorg. Med. Chem., 7, 1195-1200,(1999), wherein phosphoric acid mono(3-dodecylmercapto-2-decyloxy)-1-propyl ester and morphiline are dissolved in a mixture of water and tert-butanol (e.g., 1:1 by volume). Dicylohexylcarbodiimide (DCC) in tert-butanol is added to this solution (e.g., approximately 4 molar excess of DCC relative to phosphoric acid mono(3-dodecylmercapto-2-decyloxy)-1-propyl ester) and reaction is refluxed (e.g., 3.5 hr). Volume is reduced by evaporation and mixture cooled to cause precipitation of the phospho morpholidate.

The phospho morpholidate (e.g., 1.13 mol per mol of adenosine derivative) is prepared as an anhydrous pyridine (e.g., 23 mL/mmole adenosine derivative) and 2-chloro-9-(2'-deoxy-2'-fluoro-5'-O-phosphate-β-D-arabinofuranosyl)adenine is added with stirring, all under nitrogen. The mixture is stirred (e.g., 40° C. for at least 16 h) and then water (e.g., 4.5 mL/mmole adenosine derivative) is added and stirring continued (e.g., for 1 h). The solvent is evaporated and the product chromatographed (e.g., silica gel, eluting with a mixture of CHCl$_3$, MeOH and NH$_4$OH (aq)) to afford (2-chloro-9-(2'-deoxy-2'-fluoro-β-D-arabinofuranosyl)adenine-5'-diphosphoric acid, [3-dodecylmercapto-2-decyloxy)propyl ester as a white solid (e.g., in 20-100% yield).

EXAMPLE 5

Tablet Formulation 1.50 kg [2-Chloro-9-(2'-deoxy-2'-fluoro-β-D arabinofuranosyl)adenine]-5'-phosphoric acid-(3-dodecylmercapto-2-decyloxy)propyl ester sodium salt,
1.42 kg microcrystalline cellulose,
1.84 kg lactose,
0.04 kg Polyvinylprrolidine and
0.20 kg magnesium stearate were mixed in dry form, moistened with water and granulated. After drying the material was pressed to tablets of 500 mg weight.

EXAMPLE 6

Formulation For Injection 10.0 g kg [2-Chloro-9-(2'-deoxy-2'-fluoro-β-D arabinofuranosyl)adenine]-5'-phosphoric acid-(3-dodecylmercapto-2-decyloxy)propyl ester sodium salt were dissolved in 500 ml physiologic sodium chloride solution, filled at 5 ml in ampoules and sterilized. The solution may be applied by intravenous injection.

EXAMPLE 7

Antitumor activity of [2-Chloro-9-(2'-deoxy-2'-fluoro-β-D arabinofuranosyl)adenine]-5'-phosphoric acid-(3-dodecylmercapto-2-decyloxy)propyl ester ("nucleotide conjugate") and 2-Chloro-9-(2'-deoxy-2'-fluoro-β-D arabinofuranosyl)adenine ("nucleoside") in a human colon carcinoma xenograft model (HCT-15) in vivo The antitumor activity of the nucleotide conjugate and its corresponding nucleoside has been compared in the human colon carcinoma xenograft HCT-15 model in nude mice.

Tumor bearing mice were randomized on day 7 after HCT-15 tumor cell inoculation and were distributed to treatment groups of 9 animals per group. Treatment was started on day 8. The animals were treated intraperitoneally (ip) once daily for 5 consecutive days with the nucleotide conjugate or the nucleoside. Dosages included 50 and 25% of the Maximum Tolerable Doses (MTD's). Control animals were injected with the corresponding solvents (Vehicle 1 or 2). On day 28, the primary tumors were explanted and the tumor weights were determined. The median tumor weights are shown in Table 1.

TABLE 1

| Compound | MTD | Dose (mg/kg/injection) | Tumor weight (mg) | Tumor inhibition (%) |
|---|---|---|---|---|
| Control I (No treatment) | — | — | 592 | |
| Control II (Vehicle 1) | — | 0 | 572 | |
| Nucleoside* | 25% | 20 | 431 | 25% |
| Nucleoside* | 50% | 40 | 329 | 42% |
| Control III (Vehicle 2) | — | 0 | 669 | |

TABLE 1-continued

| Compound | MTD | Dose (mg/kg/injection) | Tumor weight (mg) | Tumor inhibition (%) |
|---|---|---|---|---|
| Nucleotide conjugate** | 25% | 63 | 257 | 62% |
| Nucleotide conjugate** | 50% | 125 | 16 | 98% |

* 2-Chloro-9-(2'-deoxy-2'-fluoro-β-D arabinofuranosyl)adenine
** [2-Chloro-9-(2'-deoxy-2'-fluoro-β-D arabinofuranosyl)adenine]-5'-phosphoric acid-(3-dodecylmercapto-2-decyloxy)propyl ester—Example 2 or 3

The antitumor efficacy of the nucleotide conjugate was significantly ($p<0.01$) higher than that of the corresponding nucleoside at both doses.

EXAMPLE 8

Antitumor activity of [2-Chloro-9-(2'-deoxy-2'-fluoro-β-D arabinofuranosyl) Adenine] -5-phosphoric acid-(3-dodecylmercato-2-decyloxy) propyl ester (nucleotide conjugate) and 2-Chloro-9-(2'-deoxy-2'-fluoro-β-D arabinofuranosyl)adenine (nucleoside) in a human breast carcinoma xenograft model (MDA-MB-231) in vivo.

The antitumor activity of nucleotide conjugate and its corresponding nucleoside has been compared in the human breast carcinoma xenograft MDA-MB-231 model in nude mice.

Tumor bearing mice were randomized on day 21 after MDA-MB-231 tumor cell inoculation and were distributed to treatment groups of 9 animals per group. Treatment was started on day 21. At this time point the animals had well vascularized tumors of about 400 mg. The animals were treated orally once daily for 2 weeks with nucleotide conjugate and its corresponding nucleoside on days 21-25 and 28-32. Doses ranged from 6.25% to 50% of the Maximum Tolerable Doses (MTD's). Control animals were treated with the solvent (vehicle) only. Median tumor volumes on day 49 are shown in Table 1.

| Compound | MTD | Dose (mg/kg/injection) | Tumor volume (mm$^3$) | Tumor inhibition (%) |
|---|---|---|---|---|
| Control | — | 0 | 3430 | |
| Nucleoside* | 6.25% | 2.5 | 1862 | 46 |
| Nucleoside* | 12.50% | 5.0 | 550 | 84 |
| Nucleoside* | 25.00% | 10.0 | 172 | 95 |
| Nucleoside* | 50.00% | 20.0 | 108 | 97 |
| Nucleotide conjugate** | 6.25% | 12.5 | 1267 | 63 |
| Nucleotide conjugate** | 12.50% | 25.0 | 196 | 94 |
| Nucleotide conjugate** | 25.00% | 50.0 | 108 | 97 |
| Nucleotide conjugate** | 50.00% | 100.0 | 51 | 99 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester The antitumor efficacy of the nucleotide was significantly ($p<0.05$) higher than that of the corresponding nucleoside at all doses

Example 9

Antitumor activity of [2-Chloro-9-(2'-deoxy-2'-fluoro-β-D arabinofuranosyl) adenine] -5-phosphoric acid-(3-dodecylmercato-2-decyloxy) propyl ester (nucleotide conjugate) and 2-Chloro-9-(2'-deoxy-2'-fluoro-β-D arabinofuranosyl)adenine (nucleoside) in a human prostate carcinoma xenograft model (PC-3) in vivo The antitumor activity of nucleoside conjugate and nucleoside has been compared in the human prostate carcinoma xenograft PC-3 model in nude mice.

Tumor bearing mice were randomized on day 7 after PC-3 tumor cell inoculation and were distributed to treatment groups of n=10 animals per group. Treatment was started on day 7. The animals were treated intraperitoneally (ip) once daily for 5 consecutive days with nucleotide conjugate or nucleoside. Dosages included 100 and 50% of the Maximum Tolerable Doses (MTD's). Control animals were treated with the corresponding solvent (vehicle) only. On day 52, the primary tumors were explanted and the tumor weights were determined. The median tumor weights are shown in Table 1.

| Compound | MTD | Dose (mg/kg/injection) | Tumor weight (mg) | Tumor inhibition (%) |
|---|---|---|---|---|
| Control (Vehicle) | — | 0 | 506 | |
| Nucleoside* | 50% | 20 | 303 | 40 |
| Nucleoside* | 100% | 40 | 202 | 60 |
| Nucleotide conjugate** | 50% | 50 | 92 | 82 |
| Nucleotide conjugate** | 100% | 100 | 64 | 87 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester The antitumor efficacy of nucleoside conjugate was significantly higher ($p<0.01$) than that of nucleoside at both doses.

Example 10

Antitumor activity of [2-Chloro-9-(2'-deoxy-2'-fluoro-β-D arabinofuranosyl)adenine] -5-phosphoric acid-(3-dodecylmercato-2-decyloxy) propyl ester (nucleotide conjugate) and 2-Chloro-9-(2'-deoxy-2'-fluoro-β-D arabinofuranosyl)adenine (nucleoside) in a human ovarian carcinoma xenograft model (SKOV-3) in vivo The antitumor activity of nucleotide conjugate and nucleoside has been compared in the human ovarian carcinoma xenograft SKOV-3 model in nude mice.

Tumor bearing mice were randomized on day 6 after SKOV-3 tumor cell inoculation and were distributed to treatment groups of 9 animals per group. Treatment was started on day 6. The animals were treated intraperitoneally (ip) once daily on day 6-10 and 13-17 with nucleotide conjugate or nucleoside. Dosages ranged between 6.25 and 100% of the Maximum Tolerable Doses (MTD's). Control animals were treated with solvent (vehicle) only. Median tumor volume at the end of the treatment period (day 17) is shown in Table 1.

| Compound | MTD | Dose (mg/kg/injection) | Tumor volume (mm³) | Tumor inhibition (%) |
|---|---|---|---|---|
| Control | — | 0 | 256 | |
| Nucleoside* | 25% | 7.5 | 162 | 37 |
| Nucleoside* | 50% | 15.0 | 108 | 58 |
| Nucleoside* | 100% | 30.0 | 126 | 51 |
| Nucleotide conjugate** | 25% | 18.8 | 144 | 44 |
| Nucleotide conjugate** | 50% | 37.5 | 108 | 58 |
| Nucleotide conjugate** | 100% | 75.0 | 63 | 75 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester The antitumor efficacy of the nucleotide conjugate was significantly higher (p<0.01) than that of the nucleoside at MTD.

Example 11

Antitumor activity of [2-Chloro-9-(2'-deoxy-2'-fluoro-β-D arabinofuranosyl)adenine] -5-phosphoric acid-(3-dodecylmercato-2-decyloxy propyl ester (nucleotide conjugate) and 2-Chloro-9-(2'-deoxy-2'-fluoro-β- arabinofuranosyl)adenine (nucleoside) in a human pancreatic carcinoma xenograft model (AspC1) in vivo The antitumor activity of nucleotide conjugate and nucleoside has been compared in the human pancreatic carcinoma xenograft AspC1 model in nude mice.

Tumor bearing mice were randomized on day 6 after AspC1 tumor cell inoculation and were distributed to treatment groups of 10 animals per group. Treatment was started on day 6. The animals were treated intraperitoneally (ip) once daily on day 6-10 and 20-23 with nucleotide conjugate or nucleoside. Dosages included 100 and 50% of the Maximum Tolerable Doses (MTD's). Control animals were treated with solvent (vehicle) only. Median tumor weight at the end of the experiment (day 30) is shown In Table 1.

| Compound | MTD | Dose (mg/kg/injection) | Tumor weight (mg) | Tumor inhibition (%) |
|---|---|---|---|---|
| Control (Vehicle) | — | 0 | 230 | — |
| Nucleoside* | 50% | 15.0 | 160 | 30 |
| Nucleoside* | 100% | 30.0 | 150 | 35 |
| Nucleotide conjugate** | 50% | 37.5 | 80 | 65 |
| Nucleotide conjugate** | 100% | 75.0 | 10 | 96 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester The antitumor efficacy of nucleotide conjugate was significantly higher (p<0.01) than that of Nucleoside at both doses.

Example 12

Antitumor activity of [2-Chloro-9-(2'-deoxy-2'-fluoro-β-D arabinofuranosyl) adenine] -5-phosphoric acid-(3-dodecylmercato-2-decyloxy) propyl ester (nucleotide conjugate) and 2-Chloro-9-(2'-deoxy-2'-fluoro-β-D arabinofuranosyl)adenine (nucleoside) in a human cervix carcinoma xenograft model (KB-3-1) in vivo The antitumor activity of nucleotide conjugate and nucleoside has been compared in the human cervix carcinoma xenograft KB-3-1 model in nude mice.

Tumor bearing mice were randomized on day 8 after KB-3-1 tumor cell inoculation and were distributed to treatment groups of 9 animals per group. Treatment was started on day 8. The animals were treated intraperitoneally (ip) once daily for 5 consecutive days (days 8-12) with nucleotide conjugate or nucleoside. Dosages included 100 and 50% of the Maximum Tolerable Doses (MTD's). Control animals were injected with solvent (Vehicle). Median tumor weight on day 29 is shown in Table 1.

| Compound | MTD | Dose (mg/kg/injection) | Tumor volume (mm³) | Tumor inhibition (%) |
|---|---|---|---|---|
| Control (Vehicle) | — | 0 | 3313 | — |
| Nucleoside* | 50% | 20 | 1059 | 68 |
| Nucleoside* | 100% | 40 | 1705 | 49 |
| Nucleotide conjugate** | 50% | 50 | 877 | 74 |
| Nucleotide conjugate** | 100% | 100 | 104 | 97 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester The antitumor efficacy of nucleotide conjugate was significantly higher (p<0.01) than that of Nucleoside at the MTD.

Summary of anti-tumor activity of the nucleotide conjugate [2-Chloro-9-(2'-deoxy-2'-fluoro-β-D arabinofuranosyl) adenine] -5-phosphoric acid-(3-dodecylmercato-2-decyloxy) propyl ester and the nucleoside 2-Chloro-9-(2'-deoxy-2'-fluoro-β-D arabinofuranosyl) adenine

| Compound | Dose (% MTD) | Tumor inhibition (%) | | | | | |
|---|---|---|---|---|---|---|---|
| | | HCT-15 | SKOV-3[a] | MDA-MB-231 | PC-3 | AspC1 | KB-3-1 |
| Nucleoside* | 6.25 | | | 46 | | | |
| Nucleoside* | 12.50 | | | 84 | | | |
| Nucleoside* | 25.00 | | 37 | 95 | | | |

-continued

| Compound | Dose (% MTD) | HCT-15 | SKOV-3[a] | MDA-MB-231 | PC-3 | AspC1 | KB-3-1 |
|---|---|---|---|---|---|---|---|
| Nucleoside* | 50.00 | 25 | 58 | 97 | 40 | 30 | 68 |
| Nucleoside* | 100.00 | 42 | 51 | | 60 | 35 | 49 |
| Nucleotide conjugate** | 6.25 | | | 63 | | | |
| Nucleotide conjugate** | 12.50 | | | 94 | | | |
| Nucleotide conjugate** | 25.00 | | 44 | 97 | | | |
| Nucleotide conjugate** | 50.00 | 62 | 58 | 99 | 82 | 65 | 74 |
| Nucleotide conjugate** | 100.00 | 98 | 75 | | 87 | 96 | 97 |

*2-Chloro-9-(2'-deoxy-2'-fluoro-β-D arabinofuranosyl)adenine
**[2-Chloro-9-(2'-deoxy-2'-fluoro-β-D arabinofuranosyl)adenine]-5-phosphoric acid-(3-dodecylmercato-2-decyloxy) propyl ester
[a]Tumor inhibition at the end of the treatment period
Type of tumors:
HCT-15): human colon carcinoma xenograft
SKOV-3: ovarian carcinoma xenograft
MDA-MB-231: human breast carcinoma xenograft
PC-3: human prostate carcinoma xenograft
AspC1: human pancreatic carcinoma xenograft
KB-3-1: human cervix carcinoma xenograft Tumor bearing mice were distributed to treatment groups of 9-10 animals per group. Treatment Treatment cycle(s)(one or two) were performed consisting of once daily intraperitoneal administrations for 5 consecutive days. Dosages were in the range of 6.25% and 100% of the Maximum Tolerated Doses (MTD's). Control animals were treated with solvent (vehicle) only, The percentage of tumor inhibition refers to the median tumor size of the vehicle treated control group and dose groups at the end of each experiment.

CONCLUSION

Superior activity of the nucleotide conjugate was found for:
HCT-1): human colon carcinoma xenograft
SKOV-3: ovarian carcinoma xenograft
MDA-MB-231: human breast carcinoma xenograft
PC-3: human prostate carcinoma xenograft
AspC1: human pancreatic carcinoma xenograft
KB-3-1: human cervix carcinoma xenograft

The invention claimed is:
1. A nucleotide derivative of formula 1

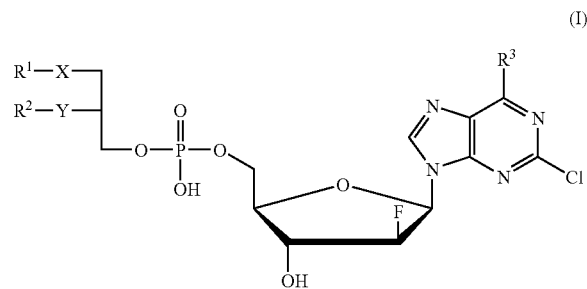

(I)

wherein
$R^1$ is a straight-chain or branched, saturated or unsaturated alkyl chain having 1-20 carbon atoms, which is unsubstituted or substituted at least once by halogen, $C_1$-$C_6$ alkoxy, $C_1$-$C_6$ alkylmercapto, $C_1$-$C_6$ alkoxycarbonyl, $C_1$-$C_6$ alkylsulfinyl or $C_1$-$C_6$ alkylsulfonyl groups;
$R^2$ is hydrogen, a straight-chain or branched, saturated or unsaturated alkyl chain having 1-20 carbon atoms, which is unsubstituted or substituted at least once by halogen, $C_1$-$C_6$ alkoxy, $C_1$-$C_6$ alkylmercapto, $C_1$-$C_6$ alkoxycarbonyl or $C_1$-$C_6$ alkylsulfonyl groups;
$R^3$ is amino or $OR^4$, wherein $R^4$ is $C_1$-$C_8$ alkyl;
X is selected from the group consisting of a sulfur atom, a sulfinyl group and a sulfonyl group;
Y is oxygen;
whereby when $R^3$ is amino, said amino group may be unsubstituted or substituted by a known amino protecting group,
their tautomers, their optically active forms and racemic mixtures, and their physiologically acceptable salts of inorganic and organic acids or bases.

2. The nucleotide derivative according to claim 1, wherein $R^1$ is a straight-chain $C_8$-$C_{15}$ alkyl group, which is unsubstituted or substituted by a $C_1$-$C_6$ alkoxy or a $C_1$-$C_6$ alkylmercapto group.

3. The nucleotide derivative according to claim 1, wherein $R^2$ represents a straight-chain $C_8$-$C_{15}$ alkyl group, which is unsubstituted or substituted by a $C_1$-$C_6$ alkoxy or a $C_1$-$C_6$ alkylmercapto group.

4. The nucleotide derivative according to claims 1, wherein $R^3$ is $OCH_3$.

5. The nucleotide derivative according to claim 1, wherein the compound is:

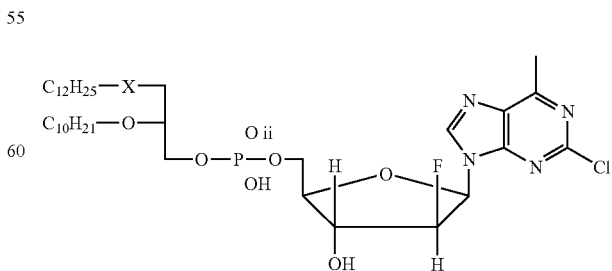

wherein X is sulfur, sulfinyl or sulfonyl.

6. The nucleotide derivative according to claim 1, wherein $R^3$ is $NH_2$.

7. The nucleotide derivative according to claim 1, wherein the compound is

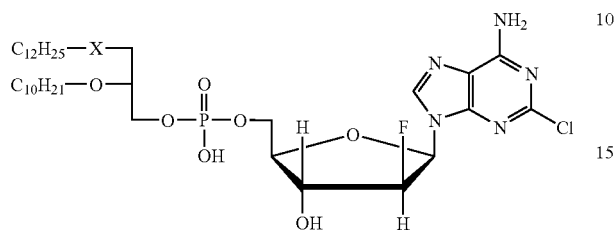

wherein X is sulfur, sulfinyl or sulfonyl.

8. A pharmaceutical composition comprising a compound according to claim 1 in combination with a pharmaceutically acceptable adjuvant or vehicle.

9. A method for treating malignant tumors comprising administering to a patient in need of such treatment an amount of a compound according to claim 1 effective to treat said tumors, wherein said tumor is a carcinoma.

10. The method of claim 9 wherein the carcinoma is selected from the group consisting of human colon carcinoma, human ovarian carcinoma, human breast carcinoma, human prostate carcinoma, human pancreatic carcinoma and human cervical carcinoma.

11. A method of synthesis of compounds of the formula Ia:

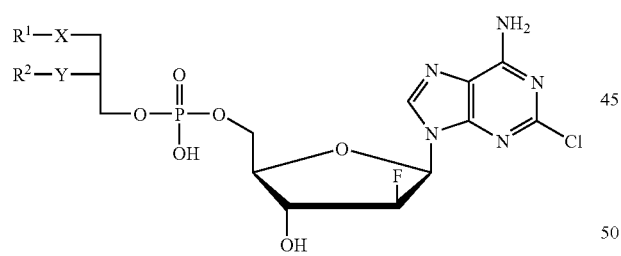

wherein $R^1$ is a straight-chain or branched, saturated or unsaturated alkyl residue having 1-20 carbon atoms, optionally mono- or polysubstituted by halogen, $C_1$-$C_6$ alkoxy, $C_1$-$C_6$ alkylmercapto, $C_1$-$C_6$ alkoxycarbonyl, $C_1$-$C_6$ alkylsulfinyl or $C_1$-$C_6$ alkylsulfonyl groups;

$R^2$ is hydrogen, a straight-chain or branched, saturated or unsaturated alkyl chain having 1-20 carbon atoms, optionally mono- or polysubstituted by halogen, $C_1$-$C_6$ alkoxy, $C_1$-$C_6$ alkylmercapto, $C_1$-$C_6$ alkoxycarbonyl or $C_1$-$C_6$ alkylsulfonyl groups;

X is selected from the group consisting of a sulfur atom, a sulfinyl group and a sulfonyl group;

Y is oxygen;

comprising:

(a) reacting 2,6-dichloroadenine with an arabinofuranosyl derivative of the formula:

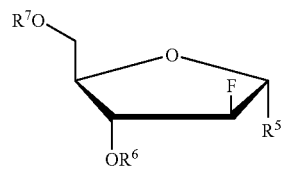

wherein $R^5$ is bromo or chloro and $R^6$ and $R^7$ are independently acetyl or benzoyl, in the presence of a base which is potassium t-butoxide or potassium t-amylate and a solvent to form the dichloropurine nucleoside derivative:

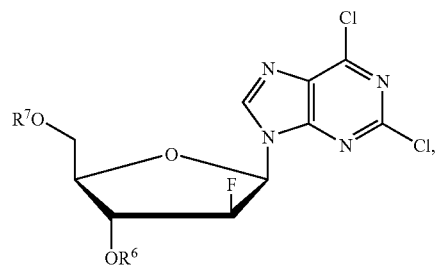

(b) subjecting said dichloro purine nucleoside derivative to basic conditions with an alkaline hydroxide and $R^4OH$ as solvent to provide for both deprotection and an aromatic nucleophilic substitution reaction to provide the 6-alkoxy-2-chloro purine nucleoside derivative of general formula IIIb:

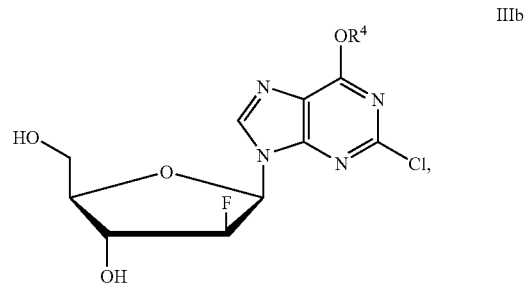

wherein $R^4$ is $C_1$-$C_8$ alkyl;

(c) reacting in an inert solvent said 6-alkoxy-2-chloro purine nucleoside derivative with the compound:

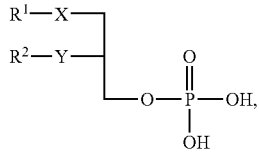

which is activated by reaction with 2,4,6-triisopropyl-benzene sulfonic chloride to provide the conjugated 6-alkoxy-2-chloro purine nucleotide derivative of general formula Ib:

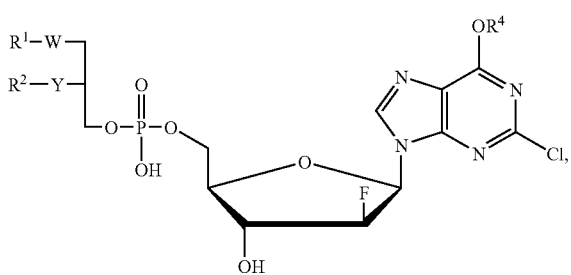

(d) subjecting said conjugated 6-alkoxy-2-chloro purine nucleotide derivative to a solution of ammonia, which provides for aminolysis, to prepare the conjugated 2-chloroadenine derivative:

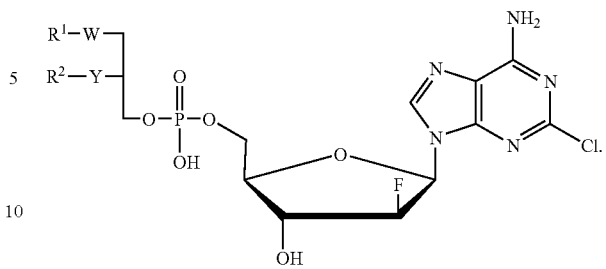

12. The method of claim 11 wherein, said hindered potassium base is potassium t-butoxide or potassium t-amylate.

13. The method of claim 11, wherein said solvent for reacting said 2,6-dichloroadenine and said arabinofuranosyl derivative is a mixture of acetonitrile, t-butanol and 1,2-dichloroethane.

14. The method of claim 11, wherein $R^4$ is methyl.

15. The method of claim 11, wherein $R^5$ is bromo.

16. The method of claim 11, wherein $R^6$ and $R^7$ are benzoyl.

17. The method of claim 11, wherein $R^1$ and $R^2$ are individually a straight-chain $C_8$-$C_{15}$ alkyl group, which is unsubstituted or substituted by a $C_1$-$C_6$ alkoxy or a $C_1$-$C_6$ alkylmercapto group.

18. The method of claim 11, wherein $R^1$ is $C_{12}H_{25}$ and $R^2$ $C_{10}H_{21}$.

19. The method of claim 11, wherein the alkaline hydroxide is sodium hydroxide.

* * * * *